United States Patent
Ma et al.

(10) Patent No.: US 11,478,150 B2
(45) Date of Patent: Oct. 25, 2022

(54) OPTICAL FIBER SENSOR

(71) Applicant: Becton, Dickinson and Company, Franklin Lakes, NJ (US)

(72) Inventors: Yiping Ma, Layton, UT (US); Azadeh Khanicheh, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 429 days.

(21) Appl. No.: 15/461,366

(22) Filed: Mar. 16, 2017

(65) Prior Publication Data
US 2017/0273565 A1 Sep. 28, 2017

Related U.S. Application Data

(60) Provisional application No. 62/314,266, filed on Mar. 28, 2016.

(51) Int. Cl.
*A61B 5/00* (2006.01)
*A61B 5/145* (2006.01)

(52) U.S. Cl.
CPC .......... *A61B 5/0084* (2013.01); *A61B 5/0059* (2013.01); *A61B 5/14503* (2013.01);
(Continued)

(58) Field of Classification Search
CPC ... A61B 5/6857; A61B 5/6856; A61B 5/6848; A61M 2025/0166
See application file for complete search history.

(56) References Cited

U.S. PATENT DOCUMENTS

| 3,789,841 A | 2/1974 | Antoshkiw |
| 4,317,445 A | 3/1982 | Robinson |

(Continued)

FOREIGN PATENT DOCUMENTS

| CN | 1184677 | 6/1998 |
| CN | 1997312 | 7/2007 |

(Continued)

OTHER PUBLICATIONS

Schneider et al: "The Fibre Fabry Perot sensor. A long-term manometry sensor for quantitative intraluminal pressure measurement of the gastrointestinal tract", Clinical Physics and Physiological Measurement, Institute of Physics Publishing, Bristol, GB, vol. 11, No. 4, Nov. 1, 1990, pp. 319-325.

*Primary Examiner* — Rajeev P Siripurapu
(74) *Attorney, Agent, or Firm* — Kirton McConkie; Whitney Blair; Kevin Stinger (57) ABSTRACT

A system to detect a position of a cannula may include a cannula, which may include a distal tip and an inner lumen. Also, the system may include an optical fiber, which may be disposed within the inner lumen of the cannula and may include a first end, a second end, and a U-shaped portion disposed between the first end and the second end. The U-shaped portion may be at least proximate the distal tip. Further, the system may include a light emitter, which may be coupled with the first end of the optical fiber, and a light receiver, which may be coupled with the second end of the optical fiber. Moreover, the system may include an electronic processor. The electronic processor may be coupled with the light receiver and configured to detect a decrease in an intensity of light received at the light receiver.

6 Claims, 4 Drawing Sheets

(52) U.S. Cl.
CPC .......... *A61B 5/6847* (2013.01); *A61B 5/6852* (2013.01); *A61B 5/7271* (2013.01); *A61B 5/746* (2013.01)

(56) References Cited

U.S. PATENT DOCUMENTS

| | | | |
|---|---|---|---|
| 4,682,895 A | 7/1987 | Costello | |
| 4,800,886 A * | 1/1989 | Nestor | A61B 5/1459 |
| | | | 356/437 |
| 5,054,882 A | 10/1991 | Riccitelli et al. | |
| 5,092,845 A | 3/1992 | Chang | |
| 5,124,130 A * | 6/1992 | Costello | G01N 21/7703 |
| | | | 356/402 |
| 5,271,398 A | 12/1993 | Schlain et al. | |
| 5,452,076 A | 9/1995 | Schopper et al. | |
| 5,460,182 A | 10/1995 | Goodman et al. | |
| 5,772,636 A | 6/1998 | Brimhall et al. | |
| 5,779,680 A | 7/1998 | Yoon | |
| 7,496,392 B2 | 2/2009 | Alarcon et al. | |
| 7,787,923 B2 | 8/2010 | Alarcon et al. | |
| 8,597,252 B2 | 12/2013 | Burkholz et al. | |
| 9,267,906 B2 | 2/2016 | Anway et al. | |
| 9,339,221 B1 | 5/2016 | Heaton et al. | |
| 9,700,697 B2 | 7/2017 | Gasparyan et al. | |
| 9,737,213 B1 | 8/2017 | Heaton, II et al. | |
| 10,850,046 B2 | 12/2020 | Isaacson et al. | |
| 2004/0127853 A1* | 7/2004 | Howell | A61M 39/045 |
| | | | 604/167.01 |
| 2006/0167405 A1* | 7/2006 | King | A61M 5/32 |
| | | | 604/65 |
| 2006/0184048 A1 | 8/2006 | Saadat | |
| 2006/0264745 A1 | 11/2006 | Da Silva | |
| 2007/0016130 A1 | 1/2007 | Leeflang et al. | |
| 2007/0293748 A1 | 12/2007 | Engvall et al. | |
| 2008/0009751 A1 | 1/2008 | Berndt | |
| 2008/0243031 A1 | 10/2008 | Seibel et al. | |
| 2008/0249487 A1 | 10/2008 | Engvall | |
| 2008/0262359 A1 | 10/2008 | Tearney et al. | |
| 2010/0081873 A1 | 4/2010 | Tanimura et al. | |
| 2010/0317964 A1 | 12/2010 | Hendriks et al. | |
| 2011/0009772 A1 | 1/2011 | Braun et al. | |
| 2011/0077477 A1 | 3/2011 | Romey et al. | |
| 2011/0255828 A1 | 10/2011 | Sudarshanam | |
| 2012/0088991 A1 | 4/2012 | Nachabe et al. | |
| 2012/0215065 A1 | 8/2012 | Mukherjee | |
| 2014/0276024 A1 | 9/2014 | Stigall et al. | |
| 2015/0196271 A1 | 7/2015 | Nair | |
| 2015/0305603 A1 | 10/2015 | Gal et al. | |
| 2015/0314105 A1* | 11/2015 | Gasparyan | A61M 5/427 |
| | | | 604/510 |
| 2017/0274184 A1 | 9/2017 | Isaacson et al. | |
| 2017/0281287 A1 | 10/2017 | Au | |

FOREIGN PATENT DOCUMENTS

| | | |
|---|---|---|
| CN | 101959470 | 1/2011 |
| CN | 102458229 | 5/2012 |
| CN | 102929070 | 2/2013 |
| CN | 103347461 | 10/2013 |
| EP | 2710974 | 3/2014 |
| JP | H05506949 | 10/1993 |
| JP | H0829207 | 2/1996 |
| JP | H08131549 | 5/1996 |
| JP | 2010523197 | 7/2010 |
| JP | 2012529332 | 11/2012 |
| JP | 2013009949 | 1/2013 |
| JP | 2013502269 | 1/2013 |
| JP | 2013542773 | 11/2013 |
| JP | 2015083140 | 4/2015 |
| KR | 20180135257 | 12/2018 |
| WO | 86/03832 | 7/1986 |
| WO | 2006/001759 | 1/2006 |
| WO | 2009/123026 | 10/2009 |
| WO | 2012/101583 | 8/2012 |
| WO | 2012/101584 | 8/2012 |
| WO | 2015/056257 | 4/2015 |
| WO | 2015/168655 | 11/2015 |
| WO | 2015/200712 | 12/2015 |

* cited by examiner

OPTICAL FIBER SENSOR

RELATED APPLICATIONS

This application claims the benefit of U.S. Provisional Patent Application No. 62/314,266, filed on Mar. 28, 2016, and entitled OPTICAL FIBER SENSOR, which is incorporated herein in its entirety.

BACKGROUND OF THE INVENTION

The present disclosure relates generally to optical fiber sensors. In particular, the present disclosure relates to devices, systems, and associated methods to detect a position of a cannula and/or a catheter tube using an optical fiber sensor. Detecting the position of the cannula and/or the catheter tube using the optical fiber sensor may be useful when inserting the cannula and/or the catheter tube into a blood vessel, such as a vein, of a patient. Detecting the position of the cannula and/or the catheter tube using the optical fiber sensor may also be useful for continuous monitoring of the position of the cannula and/or the catheter tube within the blood vessel.

Placing a cannula in a desired destination of a body of a patient may be a difficult task for a clinician in the medical field. For example, it may be difficult to place the cannula in proper position in the vein for infusion and/or blood collection. The clinician may want to advance the cannula far enough to access the blood or cerebrospinal fluid but does not want to advance the cannula too far so as to injure a wall of the vein, the spinal cord, or the spinal cord dura. Thus, it is important for the clinician to know when the cannula is located within the vein.

In some instances, in order to verify proper placement of the cannula of a catheter device in the vein, for example, the clinician generally confirms that there is "flashback" of blood into, for example, a flashback chamber associated with the catheter device. Flashback generally entails an appearance of a small amount of blood within the catheter device, which may be to the clinician.

However, the time it takes for flashback to appear in the flashback chamber is highly dependent on the gauges size of the cannula and patient venous blood pressure. For a 24G cannula at low venous pressure typical of pediatric patient, it may take more than five seconds for flashback to appear, which may not be a very useful indicator.

Accordingly, there is a need in the art for devices, systems, and methods that provide an instantaneous indication of a location of the distal tip of the cannula regardless of gauge size and patient condition. In addition, it would also be desirable for such a device to provide continuous indication of cannula location. Such devices, systems, and methods are disclosed herein.

BRIEF SUMMARY OF THE INVENTION

The present disclosure relates generally to optical fiber sensors. In particular, the present disclosure relates to devices, systems, and associated methods to detect a position of a cannula and/or a catheter tube using an optical fiber sensor. Detecting the position of the cannula and/or the catheter tube using the optical fiber sensor may be useful when inserting the cannula and/or the catheter tube into a blood vessel of a patient. Detecting the position of the cannula and/or the catheter tube using the optical fiber sensor may also be useful for continuous monitoring of the position of the cannula and/or the catheter tube within the blood vessel.

In some embodiments, a system to detect the position of the cannula may include the cannula, which may include a distal tip, an elongated tubular shaft, and an inner lumen formed by the elongated tubular shaft. In some embodiments, the system may include an optical fiber sensor (which may be referred to in the present disclosure as "the optical fiber") disposed within the inner lumen of the cannula. In some embodiments, the optical fiber may include a first end, a second end, and a U-shaped portion disposed between the first and the second end. In some embodiments, the U-shaped portion may be disposed at least proximate the distal tip. In some embodiments, the system may include a light emitter coupled with the first end of the optical fiber. In some embodiments, the system may include a light receiver coupled with the second end of the optical fiber. In some embodiments, the light receiver may be configured to convert light into an electrical signal.

In some embodiments, the system may also include an electronic processor, which may be coupled with the light receiver and may receive the electrical signal. In some embodiments, the electronic processor may be configured to detect a change in an intensity of light received at the light receiver based on the electrical signal. In particular, in some embodiments, the electronic processor may be configured to detect a decrease in the intensity of light received at the light receiver based on the electrical signal.

In some embodiments, the decrease in the intensity of light may occur in response to the optical fiber contacting blood when the cannula is inserted into the blood vessel. For example, the light emitter may emit light, which may be transmitted from the first end to the second end of the optical fiber. The intensity of the light received at the light receiver may be monitored by the electronic processor. When the cannula enters the blood vessel, blood within the blood vessel may travel into the distal tip of the cannula and contact the optical fiber, which may result in an increase in light lost from the optical fiber due to refraction. In further detail, before the optical fiber contacts blood, the optical fiber may contact air or another medium, which may have a lower refractive index than blood. Before the optical fiber contacts blood, total internal reflection or increased internal reflection may occur as light is transmitted through the optical fiber. Because a refractive index of blood may be higher than a refractive index of air and closer than the refractive index of air to a refractive index of the optical fiber, when blood contacts the optical fiber, more light may be lost from the optical fiber due to refraction and the optical fiber may become less efficient. Thus, less light may return to the light detector than in an absence of blood.

In some embodiments, the optical fiber may be configured to contact blood when the cannula is inserted in the blood vessel. In particular, in some embodiments, the U-shaped portion of the optical fiber may be configured to contact blood first, before a remaining portion of the optical fiber, when the cannula is inserted in the blood vessel. In some embodiments, prior to insertion of the cannula in the blood vessel, the optical fiber may contact air. In some embodiments, when the cannula is inserted into the blood vessel, blood may surround or immerse the optical fiber.

In some embodiments, the U-shaped portion may be disposed at least proximate the distal tip of the cannula. In some embodiments, a distal most portion of the U-shaped portion may be disposed proximal to a beveled edge of the distal tip, which may increase a likelihood that the beveled edge is fully inserted in the blood vessel when the decrease in the intensity of light is detected and/or protect the optical fiber as the cannula is inserted through the skin, fat, tissue, etc. of the patient.

In some embodiments, the optical fiber may be a homogeneous optical fiber. In these and other embodiments, the optical fiber may be without cladding so as to let light escape axially from the optical fiber, which may facilitate measurement of the decrease in the intensity of light when the optical fiber is exposed to blood.

In some embodiments, the optical fiber may be planar. In further detail, in some embodiments, the U-shaped portion, the first end, and the second end may be disposed within a same plane. In some embodiments, the first end and the second end may be parallel to each other.

In some embodiments, the U-shaped portion of the optical fiber may be the most sensitive section of the optical fiber for detecting contact with blood. In some embodiments, the first end and the second end may be twisted with respect to each other. For example, the first end and the second end may be twisted with respect to each other one, two, three, or more times to form a helical shape. By forming a helical shape, a sensitive section of the optical fiber may be increased in length beyond the U-shaped portion. The U-shaped portion and/or the helical shape may result in increased or continuous loss of light as blood contacts the U-shaped portion and/or the helical shape, thus providing an improved or continuous indication of the cannula position within the vein. If the distal tip of the cannula exits the vein, the blood flow within the cannula may stop and light may no longer be lost. Thus, the U-shaped portion and/or the helical shape of the optical fiber may provide improved or continuous indication the location or position of the cannula tip. The first end and/or the second end may be bent and/or twisted in any number of ways which may serve to increase a surface area of the optical fiber that contacts blood.

In some embodiments, the system may include an alarm. In some embodiments, the electronic processor may be configured to initiate the alarm, which may include an audible sound, a flashing light, etc. In some embodiments, the electronic processor may initiate the alarm in response to the electronic processor detecting the decrease in the intensity of the light received at the light receiver. In some embodiments, the alarm may be reusable. In some embodiments, the optical fiber may be disposable and configured to be separated at an optical connector from the alarm and/or a monitoring unit that includes the alarm. The optical connector may be disposed in any number of locations. In some embodiments, the optical connector may be disposed at a proximal end of a catheter device that includes the cannula.

The cannula may include any cannula that may be used with the optical fiber described in the present disclosure, including, but not limited to, a hypodermic needle, such as an intravenous catheter (IV) introducer needle, a peripheral intravenous catheter (PIVC) introducer needle, an epidural introducer needle, a spinal tap needle, etc. One of ordinary skill in the art will understand that the optical fiber may detect a decrease in light received at the light receiver in response to the optical fiber contacting a medium other than blood, such as, for example, cerebrospinal fluid. The medium may have a refractive index similar to blood and/or between the refractive index of air and the refractive index of the optical fiber.

In some embodiments, the system may include a catheter system, which may include a catheter device. The catheter system may include any catheter device. Exemplary catheter devices may include both straight and ported intravenous catheter devices, such as the AUTOGUARD™ shielded catheter device commercially available from Becton, Dickinson, and Company, integrated peripheral intravenous catheter devices, winged catheter devices, catheter devices with safety mechanisms, catheter devices with needle shields, blood collection sets, IV access sets such as the BD NEXIVA™ Closed Intravenous (IV) Catheter system available from Becton, Dickinson, and Company, etc.

In some embodiments, the catheter device may include a catheter adapter having a catheter tube. In some embodiments, the cannula of the catheter device may include an introducer needle. In some embodiments, the optical fiber may be disposed within the introducer needle. In some embodiments, the catheter device may include a needle hub, which may be coupled with a proximal end of the introducer needle. In some embodiments, the needle hub may be coupled with the catheter adapter. In some embodiments, the first end and the second end of the optical fiber may extend through at least a portion of the catheter device.

In some embodiments, the optical fiber may be disposed within the catheter tube such that the optical fiber contacts blood when the catheter tube is inserted in the blood vessel of the patient. In some instances, because a distal tip of the catheter tube may be proximal to the distal tip of the introducer needle when the introducer needle is inserted in the blood vessel of the patient, the catheter tube may still be outside the blood vessel. In some embodiments, the catheter tubing may be extruded over the optical fiber.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the cannula locator device, cannula locator system, and associated methods, as represented in FIGS. 1 through 8, is not intended to limit the scope of the invention, as claimed, but is merely representative of some embodiments of the invention.

Generally, this application relates to optical fiber sensors. In particular, the present disclosure relates to devices, systems, and associated methods to detect a position of a cannula and/or a catheter tube using an optical fiber sensor. Detecting the position of a distal tip of the cannula and/or the catheter tube may allow a clinician to appropriately position the distal tip of the cannula during a medical procedure, such as, for example, an intravenous infusion, blood draw, spinal tap, or epidural.

Figure 1A:
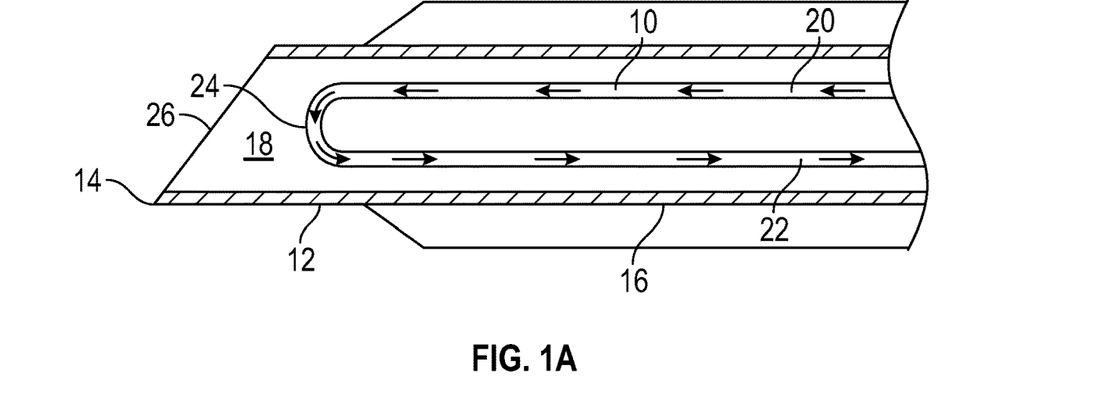
FIG. 1A is a cross-sectional view of an example portion of an optical fiber disposed within an example cannula, according to some embodiments.
Figure 1B:
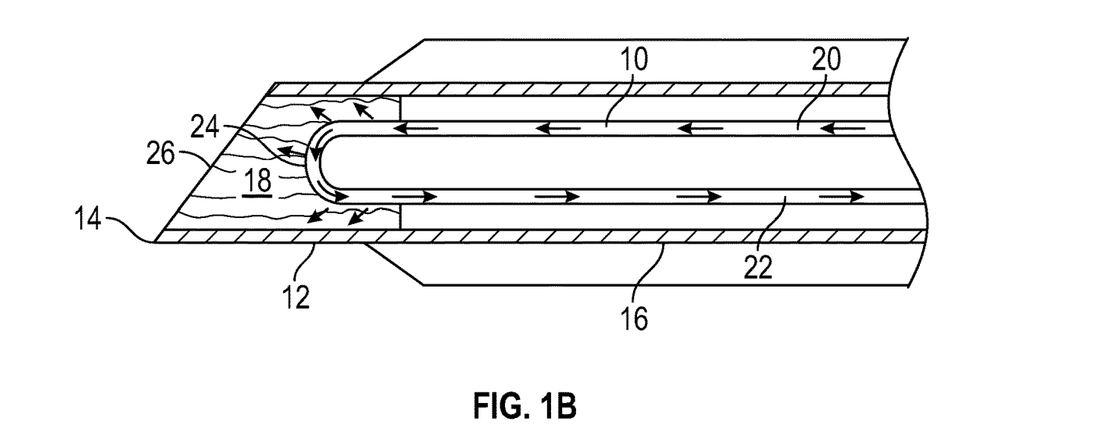
FIG. 1B is a cross-sectional view of the portion of the optical fiber of FIG. 1A in contact with blood, according to some embodiments.

FIGS. 1A-1B are cross-sectional views of a portion of an optical fiber 10 disposed within a cannula 12, according to some embodiments. In some embodiments, the cannula may include a distal tip 14, an elongated tubular shaft 16, and an inner lumen 18 formed by the elongated tubular shaft 16. In some embodiments, the optical fiber 10 may be disposed within the inner lumen 18 of the cannula 12. In some embodiments, the optical fiber 10 may include a first end 20, a second end 22, and a U-shaped portion 24 disposed between the first end 20 and the second end 22. In some embodiments, the U-shaped portion 24 may be disposed at least proximate the distal tip 14. In some embodiments, the first end 20 of the optical fiber 10 may be coupled with a light emitter (not illustrated in FIGS. 1A-1B). In some embodiments, the second end 22 of the optical fiber 10 may be coupled with a light receiver (not illustrated in FIGS. 1A-1B). One of ordinary skill in the art will appreciate that the first end 20 may be coupled with the light receiver, and the second end 22 may be coupled with the light emitter, in some embodiments.

In some embodiments, a decrease in an intensity of light received at the light receiver may occur in response to the optical fiber 10 contacting blood or another medium when distal tip 14 of the cannula 12 is inserted into the blood vessel. For example, the light emitter may emit light, which may be transmitted from the first end 20 to the second end 22 of the optical fiber. The intensity of light received at the light receiver may be monitored by an electronic processor (not illustrated in FIGS. 1A-1B). In some embodiments, when the distal tip 14 of the cannula 12 enters the blood vessel, blood within the blood vessel may travel into the distal tip 14 and contact the optical fiber 10, which may result in an increase in light lost from the optical fiber 10 due to refraction. In further detail, as illustrated in FIG. 1A, before the optical fiber 10 contacts blood, the optical fiber 10 may contact air or another medium inside the cannula 12, which may have a lower refractive index than blood. Before the optical fiber 10 contacts blood, total internal reflection or increased internal reflection may occur as light is transmitted through the optical fiber. Because a refractive index of blood may be higher than a refractive index of air and closer than the refractive index of air to a refractive index of the optical fiber 10, when blood contacts the optical fiber 10, as illustrated in FIG. 1B, more light may be lost from the optical fiber 10 due to refraction and the optical fiber 10 may become less efficient. Thus, less light may return to the light detector than in an absence of blood.

In some embodiments, the optical fiber 10 may be configured to contact blood when the cannula 12 is inserted in the blood vessel. In particular, in some embodiments, the U-shaped portion 24 of the optical fiber may be configured to contact blood first when the cannula 12 is inserted in the blood vessel. In some embodiments, prior to insertion of the cannula 12 in the blood vessel, all or a portion of the optical fiber 10 may contact air. In some embodiments, when the cannula 12 is inserted into the blood vessel, blood may surround or immerse the optical fiber 10. In some embodiments, the U-shaped portion 24 may be disposed at least proximate the distal tip 14 of the cannula 12. In some embodiments, a distal most portion of the U-shaped portion 24 may be disposed proximal to a beveled edge 26 of the distal tip 14, which may increase a likelihood that the beveled edge 26 is fully inserted in the blood vessel when the decrease in the intensity of light is detected and/or protect the optical fiber as the cannula 12 is inserted through the skin, fat, tissue, etc. of the patient.

In some embodiments, the optical fiber 10 may be a homogeneous optical fiber. In these and other embodiments, the optical fiber 10 may be without cladding so as to let light escape axially from the optical fiber 10, which may facilitate measurement of the decrease in the intensity of light when the optical fiber 10 is exposed to blood.

In some embodiments, the optical fiber 10 may be planar, as illustrated in FIGS. 1A-1B. In further detail, in some embodiments, the U-shaped portion 24, the first end 20, and the second end 22 may be disposed within a same plane. In some embodiments, the first end 20 and the second end 22 may be parallel to each other, as illustrated in FIGS. 1A-1B.

Figure 2A:
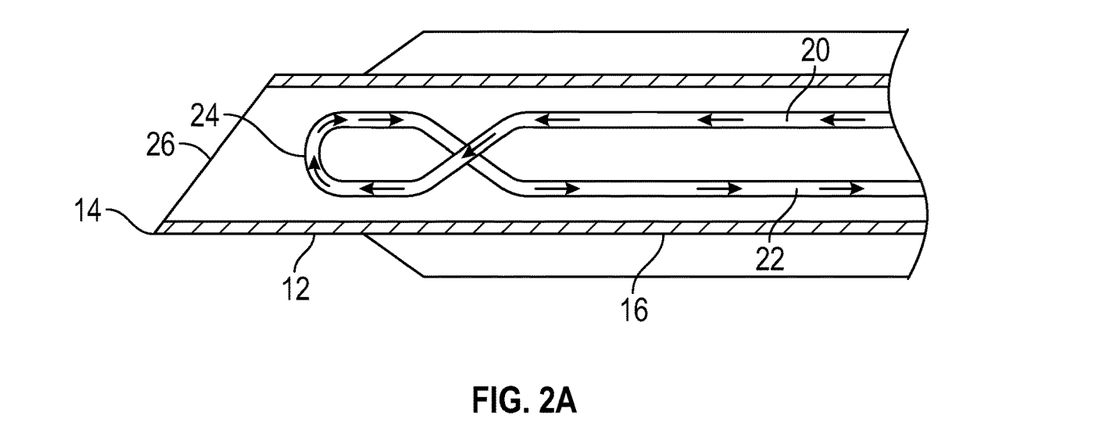
FIG. 2A is a cross-sectional view of a portion of another optical fiber disposed within the cannula of FIG. 1A, according to some embodiments.
Figure 2B:
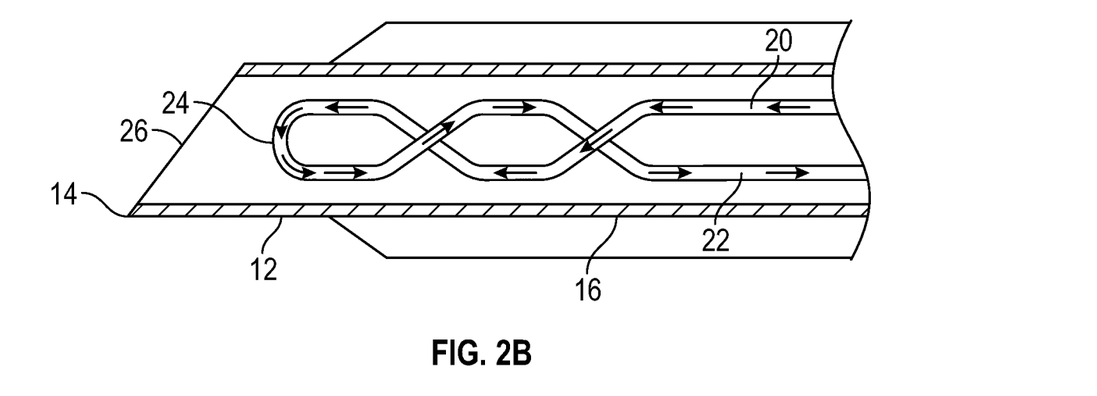
FIG. 2B is a cross-sectional view of a portion of another optical fiber disposed within the cannula of FIG. 1A, according to some embodiments.

Referring now to FIGS. 2A-2B, in some embodiments, the first end 20 and the second end 22 may be twisted with respect to each other. For example, the first end 20 and the second end 22 may be twisted with respect to each other one, two, three, or more times to form a helical shape. FIG. 2A illustrates the first end 20 and the second end 22 twisted with respect to each other one time to form the helical shape. FIG. 2B illustrates the first end 20 and the second end 22 twisted with respect to each other two times to form the helical shape. The helical shape of the optical fiber 10 may increase a length and surface area of the sensitive section of the optical fiber 10 that contacts blood, which may result in increased or continuous loss of light as light is transmitted through the optical fiber 10 in contact with blood as blood flows in the proximal direction within the cannula 12. Thus, the helical shape may provide an improved or continuous indication of the location or position of the cannula 12.

For example, when a medium contacting the optical fiber 10 changes from a first medium, for example air, to a second medium, for example blood, a loss in the intensity of light received by the light receiver may occur. A contact area between the optical fiber 10 and the second medium may increase due to the helical shape, and the loss in the intensity of light may occur along the contact area. If the first medium and the second medium have similar refractive indexes, a movement from the first medium to the second medium may be more easily detected when the optical fiber includes the helical shape. The first end 20 and/or the second end 22 may be bent and/or twisted in any number of ways that may serve to increase the surface area of the optical fiber 10 that contacts blood.

The cannula 12 may include any cannula that may be used with the optical fiber 10 described in the present disclosure, including, but not limited to, a hypodermic needle, such as an intravenous catheter (IV) introducer needle, a peripheral intravenous catheter (PIVC) introducer needle, an epidural introducer needle, a spinal tap needle, etc.

Figure 3:
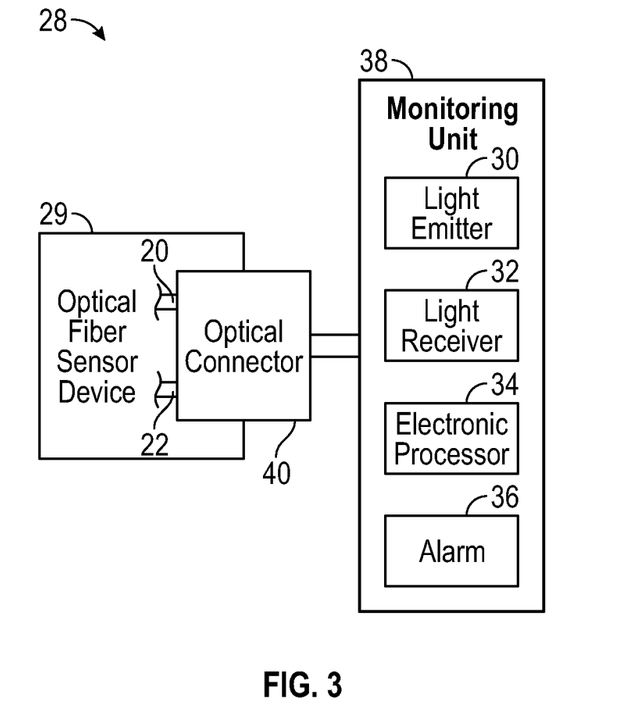
FIG. 3 is a schematic block diagram of an example system to detect a position of a cannula, according to some embodiments.

Referring now to FIG. 3, in some embodiments, a system 28 may include an optical fiber sensor device 29. In some embodiments, the optical fiber sensor device 29 may include the cannula 12 and/or the optical fiber 10. The optical fiber sensor device 29 may correspond to any number of devices that include the optical fiber 10. In some embodiments, the optical fiber sensor device 29 may include a catheter device, as will be discussed further with respect to FIG. 4. In some embodiments, the system 28 may include a light emitter 30, which may be coupled with the first end 20 of the optical fiber 10. In some embodiments, the system 28 may include a light receiver 32, which may be coupled with the second end 22 of the optical fiber 10. In some embodiments, the light receiver 32 may be configured to convert light into an electrical signal.

In some embodiments, the system 28 may also include an electronic processor 34, which may be coupled with the light receiver 32. In some embodiments, the electronic processor 34 may be configured to receive the electrical signal from the light receiver 32 and monitor an intensity of light received at the light receiver 32. In some embodiments, the electronic processor 34 may be configured to detect a change in the intensity of light received at the light receiver 32 based on the electrical signal. In particular, in some embodiments, the electronic processor 34 may be configured to detect the decrease in the intensity of light received at the light receiver 32, which may occur in response to the optical fiber 10 contacting blood, for example.

In some embodiments, the system 28 may include an alarm 36. In some embodiments, the electronic processor 34 may be configured to initiate the alarm 36, which may produce an audible sound, a flashing light, etc. In some embodiments, the electronic processor 34 may initiate the alarm in response to the electronic processor 34 detecting the decrease in the intensity of the light received at the light receiver 32. In some embodiments, the alarm 36 may be configured to sound in response to the detection of the decrease in the intensity of the light received at the light receiver 32.

In some embodiments, the alarm 36 may be reusable. In some embodiments, a monitoring unit 38 may include one or more the following: the light emitter 30, the light receiver 32, the electronic processor 34, and the alarm 36. In some embodiments, one or more of the following elements may be selectively coupled to the optical fiber 10: the light emitter 30, the light receiver 32, the electronic processor 34, the alarm 36, and the monitoring unit 38. In some embodiments, an optical connector 40 may selectively couple the optical fiber 10 to one or more of the elements. Thus, one or more of the elements may be uncoupled from the optical fiber 10 via the optical connector 4, and the optical fiber 10, the cannula 12, and/or the optical fiber sensor device 29 may be disposed of while the one or more elements may be reusable. In some embodiments, the first end 20 and the second end 22 may be coupled with a proximal end of the optical connector 40, as illustrated in FIG. 3. In some embodiments, the light emitter 30 may be coupled with the first end 20 and/or the light receiver 32 may be coupled with the second end 22 via the optical connector 40.

The optical connector 40 may be disposed in any number of locations. In some embodiments, the optical connector 40 may be disposed at a proximal end of the optical fiber sensor device 29 that includes the cannula 12. In these and other embodiments, the optical connector 40 may be disposed within the optical fiber sensor device 29. In some embodiments, the optical connector 40 may be eliminated and the optical fiber sensor device 29 may be directly coupled to the monitoring unit.

Figure 4:
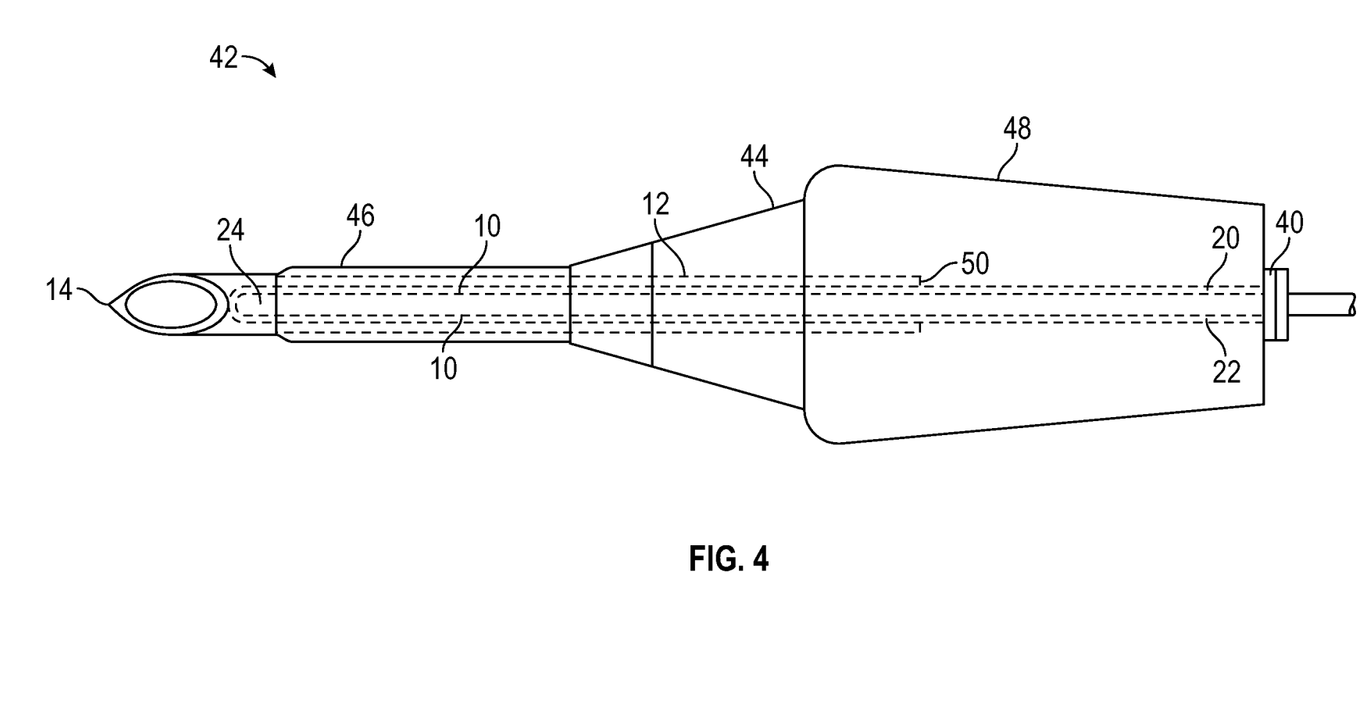
FIG. 4 is a perspective view of an example catheter device that may be included in the system of FIG. 3.

Referring now to FIG. 4, in some embodiments, the optical fiber sensor device 29 may include or correspond to a catheter device 42, an example of which is illustrated in FIG. 4. The catheter device 42 may include any number of catheter devices. Exemplary catheter devices may include both straight and ported intravenous catheter devices, such as the AUTOGUARD™ shielded catheter device commercially available from Becton, Dickinson, and Company, integrated peripheral intravenous catheter devices, winged catheter devices, catheter devices with safety mechanisms, catheter devices with needle shields, blood collection sets, IV access sets such as the BD NEXIVA™ Closed Intravenous (IV) Catheter system available from Becton, Dickinson, and Company, etc.

In some embodiments, the catheter device 42 may include a catheter adapter 44 having a catheter tube 46. In some embodiments, the cannula 12 of the catheter device 42 may include an introducer needle. In some embodiments, the catheter device 42 may include a needle hub 48, which may be coupled with a proximal end 50 of the cannula 12. In some embodiments, the needle hub 48 may be coupled with the catheter adapter 44. In some embodiments, the first end 20 and the second end 22 of the optical fiber 10 may extend through all or a portion of the catheter device 42, as illustrated in FIG. 4.

Figure 5:
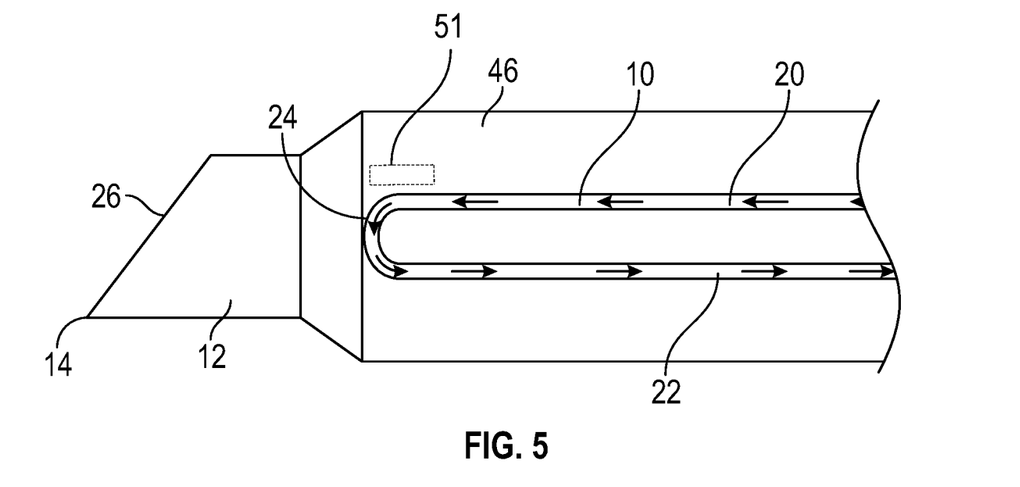
FIG. 5 is a side view of the optical fiber of FIG. 1 disposed within a wall of catheter tubing, according to some embodiments.

In some instances, because the catheter tube 46 may be proximal to the distal tip 14 of the cannula 12 when the cannula 12 is inserted in the blood vessel of the patient, the catheter tube 46 may still be outside the blood vessel when the cannula 12 is within the blood vessel. Referring now to FIG. 5, in some embodiments, the optical fiber 10 may be disposed within an outer wall of the catheter tube 46 such that the optical fiber 10 contacts blood when the catheter tube 46 is inserted in the blood vessel of the patient. Thus, the optical fiber 10 may improve detection of a position of the catheter tube 46.

The optical fiber 10 may be disposed within the outer wall of the catheter tube 46 in any number of ways. For example, the optical fiber 10 may be inserted, molded, or co-extruded into the catheter tube 46. In some embodiments, the optical fiber 10 may extend to a distal tapered portion of the catheter tube 46 and/or may be planar, as illustrated in FIG. 5. In some embodiments, the optical fiber 10 may extend to a distal edge of the catheter tube 46.

In some embodiments, the optical fiber 10 may be disposed within an inner wall of the catheter tube 46 or another portion of the catheter device 42 (not illustrated in FIG. 5). The optical fiber 10 may be disposed within the inner wall in any number of ways. For example, the optical fiber 10 may be inserted, molded, or co-extruded into the inner wall. In some embodiments, the cannula 12 may include a notch feature 51, which may define an opening in the elongated shaft 16. In some embodiments, the notch feature 51 may be configured to allow blood to flow between the distal tip 14 and the notch feature 51. In some embodiments, the blood may then flow out of the notch feature 51 and into a portion of the catheter device, such as the catheter tube 46 and/or a body of the catheter adapter 44, where the blood may contact the optical fiber 10 disposed within the inner wall.

The optical fiber 10 illustrated in FIG. 5 may include or correspond to the optical fiber 10 described in the previous figures. For example, in some embodiments, the first end 20 and the second end 22 of the optical fiber 10 may be twisted with respect to each other.

Figure 6:
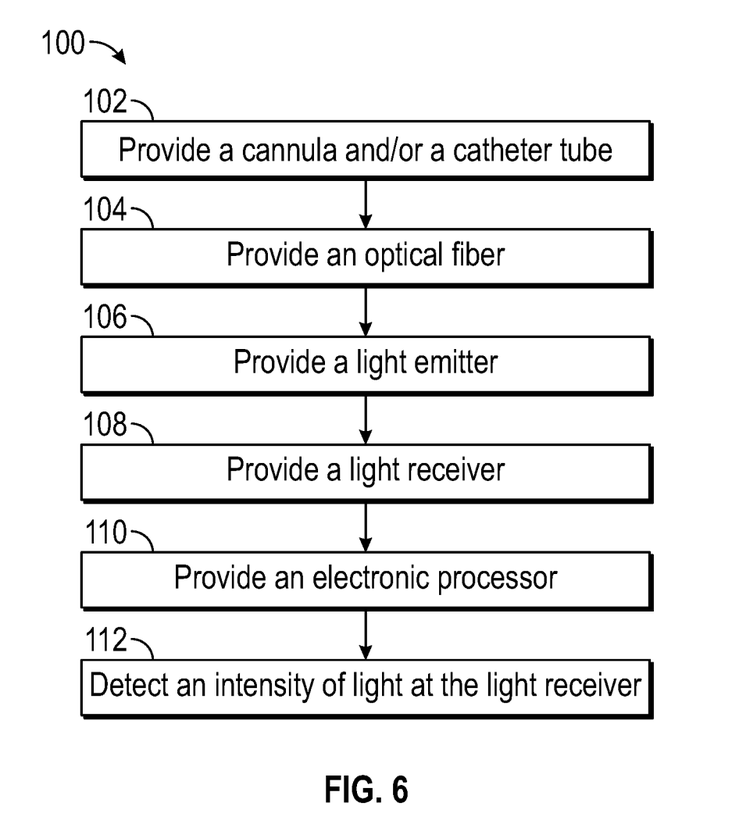
FIG. 6 is a block diagram of an example method to detect the position of the cannula, according to some embodiments.

FIG. 6 illustrates a block diagram of an example method 100 to detect the position of the cannula 12 and/or a catheter tube 46, according to some embodiments. The method 100 may begin at block 102 in which the cannula 12 and/or the catheter tube 46 is provided. In some embodiments, the cannula 12 may include the distal tip 14, the elongated tubular shaft 16, and the inner lumen 18 formed by the elongated tubular shaft 16. Block 102 may be followed by block 104.

At block 104, the optical fiber 10 may be provided. The optical fiber 10 may be disposed within the inner lumen 18 of the cannula 12, the outer wall of the catheter tube 46, and/or the inner wall of the catheter tube 46. In some embodiments, the optical fiber may include the first end 20, the second end 22, and the U-shaped portion 24 disposed between the first end 20 and the second end 22. In some embodiments, the optical fiber 10 may be disposed at least proximate the distal tip 14. Block 104 may be followed by block 106.

At block 106, the light emitter 30 may be provided. Block 106 may be followed by block 108.

At block 108, the light receiver 32 may be provided. In some embodiments, the light receiver 32 may be coupled with the second end 22 of the optical fiber 10. In some embodiments, the light receiver 32 may be configured to convert light into an electrical signal. Block 108 may be followed by block 110. Block 108 may be followed by block 110.

At block 110, the electronic processor 34 may be provided. In some embodiments, the electronic processor 34 may be coupled with the light receiver 32. Block 110 may be followed by block 112.

At block 112, an intensity of the light received at the light receiver may be detected.

Although illustrated as discrete blocks, various blocks may be divided into additional blocks, combined into fewer blocks, or eliminated, depending on the desired implementation. In some embodiments, the method 100 may include additional blocks. For example, in some embodiments, the method 100 may include inserting the cannula 12 into a blood vessel and detecting the decrease in the intensity of light received at the light receiver 32, which may occur in response to the optical fiber 10 contacting blood in the blood vessel. As another example, in some embodiments, the method 100 may include sounding the alarm 36 in response to detecting the decrease in the intensity of the light received at the light receiver 32.

In addition to the previously described embodiments of the optical fiber 10, the optical fiber 10 may be modified in any suitable manner that allows it to fulfill its intended purpose. Further, the optical fiber 10 may be used in any suitable manner. Also, in addition to the previously described embodiments of the system 28, the system 28 may be modified in any suitable manner that allows it to fulfill its intended purpose. By way of non-limiting illustration, the system 28 may not include the alarm 36. Further, in addition to the previously described embodiments of the catheter device 42, the catheter device 42 may be modified in any suitable manner that allows it to fulfill its intended purpose.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A catheter system, comprising:
    a catheter adapter having a catheter tube forming a single lumen, the catheter tube having a distal tapered portion; and
    a needle hub from which an introducer needle extends, the introducer needle having a distal tip and a notch feature, the needle hub being coupled to the catheter adapter such that the introducer needle is positioned within and extends through the single lumen to thereby position the distal tip of the introducer needle distally beyond a distal end of the catheter tube;
    wherein the catheter tube comprises an optical fiber comprising a first end, a second end, and a U-shaped portion, wherein the U-shaped portion is disposed between the first end and the second end, wherein the U-shaped portion is molded or co-extruded within an outer wall of the catheter tube and forms an outer surface and an inner surface of the catheter tube along a length of the catheter tube such that the U-shaped portion is configured to contact blood outside of the catheter tube when the catheter tube is inserted in a blood vessel and to contact blood inside of the catheter tube that flows into the distal tip of introducer needle and out through the notch feature, the U-shaped portion extended up to but not beyond the distal tapered portion of the catheter tube;
    a light emitter coupled with the first end of the optical fiber;
    a light receiver coupled with the second end of the optical fiber, wherein the light receiver is configured to convert light into an electrical signal; and
    an electronic processor coupled with the light receiver, wherein the electronic processor is configured to detect a decrease in an intensity of the light received at the light receiver when the distal end of the catheter tube is inserted into a patient's vasculature after the distal tip of the introducer needle has been inserted into the patient's vasculature.

2. The catheter system of claim 1, wherein the optical fiber is a homogenous optical fiber.

3. The catheter system of claim 1, wherein the decrease in the intensity of light occurs in response to the optical fiber contacting the blood.

4. The catheter system of claim 3, further comprising an alarm, wherein the alarm is configured to sound in response to detecting the decrease in the intensity of the light received at the light receiver.

5. The catheter system of claim 4, wherein the alarm is reusable, wherein the optical fiber is disposable and configured to be separated from the alarm at an optical connector disposed at a proximal end of the catheter system.

6. The catheter system of claim 1, wherein the U-shaped portion, the first end, and the second end do not include cladding.

* * * * *